United States Patent [19]

Lu et al.

[11] Patent Number: 4,808,411

[45] Date of Patent: Feb. 28, 1989

[54] ANTIBIOTIC-POLYMER COMPOSITIONS

[75] Inventors: Mou-Ying F. Lu, Lake Bluff; Saul Borodkin, Libertyville Township, Lake County, both of Ill.

[73] Assignee: Abbott Laboratories, Abbott Park, Ill.

[21] Appl. No.: 58,499

[22] Filed: Jun. 5, 1987

[51] Int. Cl.$^4$ ............................ A61K 9/28; A61K 9/16
[52] U.S. Cl. .................................... 424/441; 424/489; 424/494; 424/495; 424/496; 424/497
[58] Field of Search ............... 424/441, 469, 470, 480, 424/482, 489, 494, 495, 496, 497

[56] References Cited

U.S. PATENT DOCUMENTS

| | | | |
|---|---|---|---|
| 4,289,751 | 9/1981 | Windheuser | 424/44 X |
| 4,649,043 | 3/1987 | Urquhart et al. | 424/469 |
| 4,684,534 | 8/1987 | Valentine | 424/441 X |

*Primary Examiner*—Michael Lusignan
*Attorney, Agent, or Firm*—Steven F. Weinstock; Edward H. Gorman, Jr.

[57] ABSTRACT

Compositions which comprise a complex of carbomer (acrylic acid polymers) and erythromycin or a derivative thereof such as 6-O-methylerythromycin, are disclosed. The compositions provide nontoxic, palatable dry and liquid dosage forms for oral administration.

16 Claims, No Drawings

ANTIBIOTIC-POLYMER COMPOSITIONS

TECHNICAL FIELD

This invention relates to oral dosage forms for erythromycin and derviatives.

BACKGROUND ART

For ease and safety of administration, many prescription and non-prescription drugs are provided in the form of capsules and tablets for oral administration. However, patients at the extremes of age, children and the elderly, often experience difficulty in swallowing solid oral dosage forms. For these patients, drugs are commonly provided in liquid dosage forms such as solutions, emulsions and suspensions. These dosage forms usually permit perceptible exposure of the active drug ingredient to the taste bud, which gives rise to another problem. Many drugs have unpleasant tastes, and in particular are often extremely bitter. As a consequence, unless measures are taken to make the liquid dosage forms palatable, patient compliance with the prescribed regimen of treatment will suffer. Measures to make liquid dosage forms palatable include a variety of approaches. The use of relatively insoluble salts of the parent drug results in less exposure of drug in perceptible form in the mouth. Suspensions of very small coated granules of the drug prevent release of the drug in the mouth and provide a taste-hiding effect. Syrups of sugar, with or without flavoring, are often sufficient to mask the taste of the drug. Nevertheless, some drugs have such pronounced bitterness or other physicochemical characteristics that conventional approaches to flavor masking and/or hiding are unsuccessful. This is particularly problematic where the drug in question has extensive applicability in treatment of diseases of children or the elderly.

Erythromycin has a bitter taste and is particularly useful in treatment of common pediatric infections of the middle ear and upper respiratory tract, as well as certain forms of pneumonia which afflict the elderly. Acceptably palatable liquid oral dosage forms of this drug have been developed, primarily using esters and other prodrug forms of the molecule. However, such ester forms can markedly alter the pharmacokinetics and total availability of the drug in vivo. Therefore, a need exists for additional palatable oral dosage forms for erythromycin, and particularly for the base form of the drug. In addition, it has now been observed that at least one erythromycin derivative under development, 6-O-methyl erythromyin, has such pronounced bitterness that conventional approaches have been unsuccessful in development of a palatable liquid oral dosage form of this drug. Accordingly, a particular need exists for new approaches to masking or hiding the taste of bitter erythromycin derivatives.

DISCLOSURE OF THE INVENTION

This invention provides compositions comprising from about 25% to about 90% of erythromycin or a derivative thereof, and from about 10% to about 75% of a carbomer. These compositions provide palatable dosages of the antibiotic yet have pharmacokinetic properties which are substantially equivalent to commercially available tablets and capsules.

Erythromycin and its derivatives are compounds of the formula

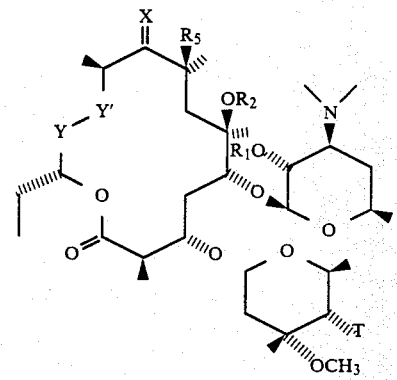

where $R_1$ is selected from hydroxyl, acyl of 2 to 20 carbon atoms, or trimethylsiloxyl, $R_2$ is hydrogen or methyl, T is hydrogen, —OH, alkoxy of 1 to 3 carbon atoms, —$OCOR_3$ or —$OCONR_3R_4$ where $R_3$ and $R_4$ are independently selected from hydrogen or alkyl of 1 to 12 carbon atoms, $R_5$ is hydrogen or halogen, X is O= or $R_6ON$= where $R_6$ is $C_1$ to $C_8$ substituted or unsubstituted alkyl, alkaryl or aryl and Y—Y' is

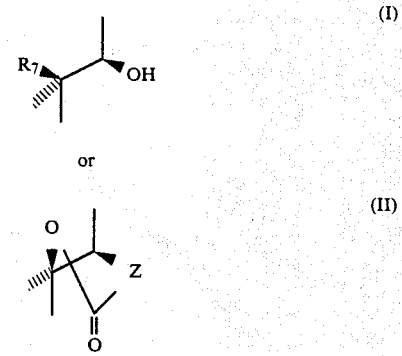

where $R_7$ is hydrogen or hydroxyl and Z is O= or $R_8N$= where $R_8$ is hydrogen, hydroxy, alkyl, alkoxy, substituted alkyl, aryl, sustituted aryl, acyl, or sulfonyl, and pharmaceutically acceptable salts and esters thereof.

The term alkyl is used herein to mean straight, branched chain and alicyclic radicals, including, but not limited to methyl, ethyl, n-propyl, isopropyl, cyclopropyl, n-butyl, sec-butyl, isobutyl, tert-butyl, cyclohexyl, cyclohexylethyl, and the like.

The term aryl is used herein to mean substituted and unsubstituted aromatic radicals, including, but not limited to phenyl, phenethyl, benzyl and the like.

By "substituted" alkyl or aryl is meant alkyl or aryl groups as defined above but in which one or more hydrogen atoms is replaced by a heteroatomic functional group such as amino, imino, halo, alkoxy, nitro, acetoxy, acetamido, hydroxy, cyano, and the like.

By "alkaryl" herein is meant a substituted or unsubstituted aromatic ring group appended to an alkyl radical as defined above, including, but not limited to benzyl, halobenzyl, nitrobenzyl, alkylbenzyl, alkoxybenzyl, phenethyl and the like.

The term "alkoxy" is used herein to mean straight and branched chain oxygen ether radicals, including, but not limited to methoxy, ethoxy, isopropoxy, n-butoxy, sec-butoxy, isobutoxy, tert-butoxy, and the like.

The term acyl is used herein to mean straight or branched chain carbonyl radicals, including but not limited to, formyl, acetyl, propionyl, butyryl, isobutyryl and the like.

By "pharmaceutically acceptable" is meant those compounds which are, within the scope of sound medical judgment, suitable for use in contact with the tissues of humans and lower animals without undue toxicity, irritation, allergic response, and the like, in keeping with a reasonable benefit/risk ratio, and effective for their intended use in the chemotherapy and prophylaxis of antimicrobial infections.

The carbomers employed in this invention are acrylic acid polymers which are commercially available from the B. F. Goodrich company and others. The average equivalent weight is 76, while the molecular weight is approximately 3 million. They have the general formula

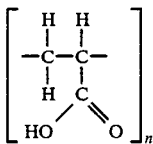

where n is from about 10,000 to about 60,000. A preferred material is official in the U.S. Pharmacopoeia as carbomer 9_4P. This material is classified as a water soluble resi.. .id has been used in other pharmaceutical preparations for its thickening and suspending properties. An aqueous dispersion of carbomer 934P has a pH of 2.8 to 3.2. In its presolvated state, carbomer is a tightly coiled molecule and its thickening properties are limited. When dispersed in water, the molecule becomes hydrated and uncoils to some extent. However, to further uncoil the molecule and generate high viscosity solutions, neutralization to a polyanionic state with a suitable base such as sodium hydroxide is required. While not intending to be limited by theory, the composition of this invention involving the combination of carbomer with erythromycin or its derivatives may involve such uncoiling.

The compositions of this invention can be prepared by dispersing the erythromycin compound in a suitable organic solvent such as ethanol or acetone, and dispersing the carbomer separately in ethanol, mixing the two solutions slowly to allow formation of the desired reaction product, evaporating most of the organic solvent and diluting the solution with water. The reaction product can be recovered by filtration and reduced to dryness. Alternatively, the composition may also be prepared by blending or slurrying a mixture of the erythromyin or derivative and the carbomer in a limited amount of organic solvent, followed by evaporation and drying. This latter process eliminates the need for a separate filtration step. Again, while not intending to be limited by theory, the reaction product is believed to be held together by both ionic attraction between the amine group of the erythromycin compound and the carbonyl group of the carbomer, and the gel properties of the insoluble carbomer. This is important for both stability of the drug and palatability of the composition. The lower the ratio of active drug to carbomer (lower the potency), the lower the drug concentration which can be leached from the complex in water (solubility). This is illustrated in the following table and is believed to be due to the larger number of anionic carboxylate sites on the polymer per cationic drug molecule.

TABLE I

| Composition | Potency (%) | pH | Solubility (ug/ml)* |
|---|---|---|---|
| Erythromycin | 100 | 8.24 | 2120 |
| Erythromycin | 100 | 7.72 | 12220 |
| Ery/carbomer | 82.3 | 7.94 | 660 |
| Ery/carbomer | 69.7 | 7.00 | 110 |
| Ery/carbomer | 61.3 | 6.75 | 80 |
| 6-O—Methyl-ery | 100 | 7.98 | 134 |
| 6-O—Methyl-ery | 100 | 7.00 | 1650 |
| 6-O—Methyl-ery | 100 | 6.20 | 7000 |
| 6-O—Me—ery/carbomer | 78.1 | 6.69 | 51 |
| 6-O—Me—ery/carbomer | 69.8 | 6.94 | 22 |
| 6-O—Me—ery/carbomer | 61.5 | 6.56 | 10 |

*The solubility reported is the concentration of drug measured in solution after material providing approximately 20 mg/mL active drug has been stirred for 24 hours in water. Buffer solution was used when pure drugs were tested.)

This provides for minimal dissolution of the erythromycin compound in a non-ionic aqueous medium such as a suspension. When ingested, the erythromycin compound is released from the complex slowly enough to avoid a significant perception of bitterness in the mouth. In the gastrointestinal tract, the carbomer composition as such cannot be absorbed because of its high molecular weight and large molecular size. Instead, the ionic environment causes liberation of the erythromycin compound for absorption into the blood stream, while the carbomer portion passes through the gut intact. In addition, since drug degradation occurs primarily in the aqueous phase, reduced dissolution enhances the stability of the drug in the dosage form.

The antibiotic/carbomer complexes of this invention can be employed in dry form, preferably in the form of particles. Such particles can be mixed with foods or beverages, can be used to prepare liquid suspensions for oral administration, or can be formed into conventional whole or chewable tablets for oral administration. In forming tablets, conventional pharmaceutically acceptable tableting agents, including lubricants, binders, disintegrants, excipients, microcrystalline cellulose, starches, waxes, gums, silicates, polymers and other minerals well known to the tableting arts can be employed.

Preferably, fine particles having average diameters smaller than 40 mesh (420 microns) will be employed. For use in a pediatric suspension, for example, a mean particle diameter of less than 50 mesh (297 microns) will be desirable. In some products, the particles will be larger, having a mean diameter of less than 10 mesh (2000 microns), or more preferably less than 1000 microns (about 16 mesh).

To further reduce dissolution of the active drug in the mouth, the complexes provided in accordance with this invention can be polymer coated. A variety of polymeric materials can be employed. Non-limiting examples of such materials include ethyl cellulose, hydroxypropyl cellulose, hydroxypropylmethylcellulose, polyvinyl acetate phthalate, cellulose acetate phthalate, hydroxypropylmethylcellulose phthalate, and shellac, as well as numerous other polymers familiar to those of ordinary skill in the pharmaceutical arts. Such other polymers commonly known by trade names include the Eudragit ® E-100, S-100 and L-100 polymers, available from the Rohm and Haas Company. Most preferable is hydroxypropylmethylcellulose phthalate.

The use of pH sensitive coatings offer advantages in addition to taste coverage. A coating insoluble at neutral pH, but soluble in acid (e.g. Eudragit ® E-100) can give complete taste protection in the neutral pH of the mouth, while still allowing rapid dissolution in the strongly acidic stomach contents after swallowing. Conversely, an enteric coating can be insoluble in acid or water while dissolving in a neutral buffer above pH 5 or 6. This offers the opportunity to prepare a suspension of coated antibiotic/carbomer that remains intact in the formulation yet rapidly liberates the antibiotic in the intestine. This is particularly useful for acid labile forms of erythromycin and derivatives, such as erythromycin base. Such drugs remain protected from the hostile environment of the stomach, but are rapidly dissolved in the higher pH of the intestinal tract.

INDUSTRIAL APPLICABILITY

The following examples illustrate the preparation and use of the compositions of this invention, without intending to be limitative thereof.

EXAMPLE 1

One hundred grams of erythromycin were dissolved in 500 ml of USP ethanol and 20 g of carbomer 934P was slurried in 600 ml ethanol separately at room temperature. The carbomer slurry was added to the erythromycin solution slowly at room temperature. The mixture was stirred for 1 hour until it becomes very smooth. The complex was crystallized by slowly pouring the slurry into about 6 l of deionized water. After 30 minutes the crystals were filtered through Whatman #41 paper with vacuum and washed with 8 liters of water. The potency as determined by colorimetric assay was 71% erythromycin. The solubility obtained by slurrying 200 mg in 10 ml of water for 24 hours was 56 micrograms erythromycin per ml solution.

EXAMPLE 2

Five grams of erythromycin was mixed dry with one gram of carbomer in a 50 ml Erlenmeyer flask. Six ml of acetone was added and the mixture was stirred for 3 hours at room temperature with a magnetic stirring bar after stoppering the flask. The stopper was removed and the acetone was allowed to evaporate while maintaining stirring. The composition was then dried at 40 degrees under vacuum. The calculated potency was 75% erythromycin. The solubility obtained by slurring 200 mg in 10 ml water for 24 hours was 360 micrograms erythromycin per ml solution.

EXAMPLE 3

Fifteen grams of 6-O-methylerythromycin were dissolved in a mixture of 200 ml acetone and 270 ml ethanol. Nine grams of carbomer 934P were slowly added with constant mixing and the slurry was stirred for 30 minutes until the mixture was uniform. While stirring, 1.9 liters of water was added and the resultant precipitate was stirred an additional 30 minutes. The solids were separated by filtration through a Whatman #1 paper with vacuum. This was then washed with 3.5 liters of water, and the damp cake was passed through a 30-mesh screen. The solids were then dried in a vacuum oven at 40 degrees. The potency determined by colorimetric assay was 63%. The solubility obtained in slurrying 200 mg in 10 ml water for 24 hours was 20 micrograms 6-O-methylerythromycin per ml solution.

EXAMPLE 4

Twelve grams of 6-O-methylerythromycin was mixed dry with 12 grams of carbomer in a Hobart mixer. To this was slowly added with mixing a solution of 8 grams of 6-O-methylerythromycin in 200 ml acetone over approximately a one hour period. The acetone was allowed to evaporate during the addition so as to keep the mixture always damp. After an additional hour of stirring, the composition was dried in a vacuum oven at 50 degrees. The potency determined by HPLC assay was 58%. The solubility obtained by slurrying 200 mg in 10 ml water for 24 hours was 34 micrograms 6-O-methylerythromycin per ml solution.

EXAMPLE 5

One hundred grams of milled erythromycin/carbomer composition prepared according to the procedure described in example 1 was added to a laboratory scale Glatt air suspension coater with 0.3 grams of magnesium stearate. The particles were coated using a coating solution composed of 18 grams hydroxypropylmethyl cellulose phthalate (HP-55), 2 grams castor oil, 130 grams acetone, 130 grams alcohol and 20 grams water. The conditions included a 0.6 mm nozzle, 18 psi atomizing air pressure, inlet air temperature of 60 degrees, and outlet air temperature of 40 degrees. The 40-60 mesh fraction was separated and 27 grams were furter coated with 20 ml of the coating solution. The potency of the coated 40-60 mesh particles was 63% based on colorimetric assay.

EXAMPLE 6

Using a laboratory scale Glatt air suspension coater, 13.5 grams of 40 to 80 mesh range 6-O-methylerythromycin prepared according to the procedure described in Example 4 was mixed with 86.5 grams 35-40 mesh non-pareil beads. The particles were coated using a coating solution composed of 15 g hydroxypropylmethyl cellulose phthalate (HP-55), 1 g castor oil, 75 ml acetone, 75 ml alcohol, 10 ml water and 200 mg of a dye. Settings for the coater included 1.0 mm nozzle, column height of 1.8 cm, spraying pressure of 15 psi, inlet air temperature of 60 degrees, and outlet air temperature of 43 degrees. The yield of particles below 40 mesh was 9.5 grams. The potency as determined by HPLC assay was 48% 6-O-methylerythromycin.

EXAMPLE 7

Sixty-four milligrams Keltrol ™ (xanthan gum) and 28 grams of sucrose were blended and added slowly to 16.8 grams of water, and the mixture was stirred until the Keltrol was fully hydrated. To this was added 1.5 grams of coated erythromycin/carbomer made according to the procedure described in example 5. Based on the calculated potency of the coated composition the suspension was calculated to contain 24 mg erythromycin per ml.

EXAMPLE 8

Twenty-three milliliters of a suspension was prepared by adding a blend of 37 mg Keltrol and 16.1 grams of sucrose to 9.7 gram of water and stirring until the Keltrol is fully hydrated. To this was then added 797 mg of coated 6-O-methylerythromycin/carbomer made according to the procedure described in example 6. Based on the calculated potency of the coated particles, the suspension was calculated to contain 100 mg 6-O-methylerythromycin per 5 ml suspension.

EXAMPLE 9

One suspension of coated erythromycin/carbomer prepared as described in example 7 and two suspensions of 6-O-methylerythromycin prepared as described in example 8. These suspensions were evaluated for bitter taste over a period of several weeks while stored at refrigerator (5° C.) conditions. Sample size was 3 mL. Both the initial taste and aftertaste were determined.

A=coated erythromycin/carbomer suspension according to Example 7.
B=6-O-methylerythromycin/carbomer suspension according to Example 8.
C=6-O-methylerythromycin/carbomer suspension according to Example 8

|  | Time at 5° C. | Initial (<10 sec) | Bitterness 1 min | 5 min | 15 min |
|---|---|---|---|---|---|
| Susp A | 0 | Absent | Moderate | String | Slight |
|  | 1 wk | Absent | Moderate | Strong | Slight |
|  | 2 wks | Threshold | Moderate | Strong | Slight |
|  | 4 wks | V. Slight | Moderate | Strong | Slight |
| Susp B | 0 | Absent | Slight | Moderate | Slight |
|  | 1 wk | Absent | Slight | Moderate | Slight |
|  | 2 wks | Absent | Moderate | Moderate | Slight |
|  | 4 wks | Absent | Moderate | Strong | Slight |
| Susp C | 0 | Absent | Slight | Moderate | Slight |
|  | 1 wk | Absent | Slight | Moderate | Slight |
|  | 2 wks | Absent | Slight | Moderate | Slight |
|  | 4 wks | Threshold | Slight | Moderate | Slight |

EXAMPLE 10

A series of suspensions prepared as described in example 8 using both uncoated and coated 6-O-methyleythromycin/carbomer prepared according to the Examples indicated below were evaluated on a more quantitative basis by a trained taste panel. At the time of tasting, all suspensions were at room temperature. A 1 to 3 ml well mixed sample was held in the mouth for 5 to 10 seconds, spat out, and the intensity of the bitterness level recorded for the initial taste (I). The intensity of the bitterness level after 60 seconds was recorded as the aftertaste (AT). The mouth was cleared with unsalted crackers and tap water at room temperature before proceeding with the next sample. A numerical scale was used to record the intensity of bitterness:
  0=Tasteless
  0.5=Very slight
  1=Slight
  1.5=Slight to Moderate
  2=Moderate
  2.5=Moderate to Strong
  3=Strong

| Form | Potency | Example | Bitterness Measurements Initial (Aftertaste) Initial | Storage at 5° C. 6 Days | 14 days |
|---|---|---|---|---|---|
| Uncoated | 62% | 3 | 0 (2) | 0.5 (2) | 1 (2) |
| Coated | 57% | 6 | 0 (0) | 0 (0) | 0 (0) |
| Uncoated | 70% | 3 | 1.5 (2) |  |  |
| Uncoated | 80% | 3 | 2 (3) |  |  |
| Coated | 72% | 6 | 0 (2) | 0.5 (2) | 1 (2) |
| Uncoated | 58% | 4 | 0 (1) |  |  |
| Coated | 52% | 6 | 0 (0) |  |  |

EXAMPLE 11

A series of bioavailability studies were run with different presentations of erythromycin/carbomer in dogs to determine the extent of absorption. Each form in the series was tested on three dogs. All dogs were faster overnight, and histamine was administered one hour prior to dosing with the test composition to assure an acid stomach environment. A sample of the test composition containing 250 mg of drug was administered to each dog. Blood samples were drawn and assayed using a standard microbiological assay. All dogs were fed after the last sample. A reference composition consisting of a conventional suspension of erythromycin ethylsuccinate was also included in the study. Results were as follows:

| Form Administered | Example | AUC 0–8 hrs. (ug/ml × hr) Mean (SD) | $C_{max}$ (ug/ml) | $T_{max}$ (hr) |
|---|---|---|---|---|
| Capsules (>30 mesh) | 1 | 1.85 (1.84) | 1.26 | 0.67 |
| Capsules (30–60 mesh) | 1 | 5.85 (0.10) | 2.24 | 0.50 |
| Capsules (100–120 mesh) | 1 | 2.61 (1.07) | 1.06 | 0.67 |
| Suspension (uncoated) | 7 | 1.41 (1.33) | 1.40 | 0.50 |
| Suspension (uncoated) | 7 | 2.70 (30.5) | 1.40 | 0.50 |
| Capsules (coated) | 5 | 1.78 (0.70) | 0.82 | 1.50 |
| Reference suspension |  | 0.65 (0.20) | 0.25 | 1.17 |

The results indicate that all forms of erythromycin/carbomer provide somewhat better absorption and blood levels in dogs than the conventional product used in suspension, erythromycin ethylsuccinate.

EXAMPLE 12

Bioavailability studies using 6-O-methylerythromycin were performed in dogs using 3-dog series. All dogs were fasted overnight, and histamine was administered one hour prior to dosing with the test composition. An quantity of the test composition containing 250 mg of 6-O-methylerythromycin was administered to each dog. Blood samples were drawn and assayed using a standard microbiological assay. All dogs were fed 12 hours after dosing. Results were as follows:

| Form | AUC 0–8 hrs. (ug/ml × hr) Mean (SD) | $T_{max}$ (hr) (SD) | $C_{max}$ (ug/ml) (SD) |
|---|---|---|---|
| Pure (powder) | 43.5 (27.5) | 1.33 (0.47) | 5.37 (4.76) |
| Drug/carbomer capsule (78% potency) | 56.2 (38.5) | 2.00 (0.82) | 4.47 (3.10) |
| Drug/carbomer suspension (78% potency) | 57.2 (10.6) | 1.67 (0.24) | 7.46 (1.40) |
| Drug/carbomer suspension (70% potency) | 58.6 (23.2) | 1.67 (0.58) | 6.08 (1.91) |
| Drug/carbomer suspension (62% potency) | 67.1 (32.6) | 1.83 (1.26) | 6.09 (3.31) |

Bioavailability from the combination dosage forms was consistently good in all studies. All studies using the combination of drug and carbomer gave higher AUCs than the drug alone, although this does not necessarily imply a true advantage for the combination.

EXAMPLE 13

A 3-way complete crossover study in 9 dogs was run to assess quantitative bioavailability from suspensions of both uncoated and coated 6-O-methylerythromycin/carbomer. The formulations tested were (A) 6-O-methylerythromycin pure drug in capsules (100 mg each); (B) uncoated particles of 6-O-methylerythromycin/carbomer prepared by the method described in example 3 and incorporated into a suspension (100 mg drug per 5 ml) as described in example 8; and (C) coated particles of 6-O-methylerythromycin/carbomer prepared as described in example 6 and incorporated into a suspension (100 mg/5 ml) as in example 8. After overnight fasting, histamine was injected, followed in one hour by a 100 mg dose of the appropriate formulation. Blood samples were obtained periodically for 8 hours and assayed by a standard microbiological method. As shown in the following table, bioavailability was very similar for the uncoated and coated 6-O-methylerythromycin/carbomer and both suspension products gave somewhat better availability than the pure drug:

| | | Mean (S.D.) | |
|---|---|---|---|
| Formulation | $T_{max}$ (hr) | $C_{max}$ (ug/ml) | AUC(mcg/ml × hr) (ug/ml × hr) |
| A | 3.0 (1.6) | 1.509 (0.646) | 8.76 (3.81) |
| B | 2.0 (0.9) | 2.273 (0.578) | 12.04 (2.86) |
| C | 2.8 (0.8) | 2.188 (0.614) | 12.19 (3.40) |
| | | Significant differences | |
| (P 0.05) | none | B, C > A | B, C > A |

EXAMPLE 14

A human bioavailability study was run to compare the bioavailability of both uncoated and coated erythromycin/carbomer given as suspensions to erythromycin base. The study was a complete crossover single dose study using 24 human volunteers who were fasted overnight before dosing with 250 mg erythromycin. The formulations utilized were (A) uncoated erythromycin/carbomer prepared as described in example 1 and incorporated into a suspension containing 250 mg erythromycin per 5 ml; (B) coated erythromycin/carbomer prepared as described in example 5 and incorporated into a suspension containing 250 mg per 5 ml; and (C) a commercial particle coated erythromycin base capsule (Eryc TM) containing 250 mg erythromycin in 2 capsules, used as the control. Blood samples were collected periodically for 10 hours after the dose was administered and the serum assayed for erythromycin using a standard microbiological assay. The following table summarizes the principal results:

| Formulation | Mean $C_{max}$, mcg/ml | Mean (Std Dev) Area Under Curve mcg/ml × hr |
|---|---|---|
| A | 0.53 | 1.65 (1.76) |
| B | 1.19 | 3.41 (1.27) |
| C | 1.34 | 3.83 (1.35) |

Statistical analysis of the study showed there was no significant difference in bioavailability between coated erythromycin/carbomer (B) and particle coated erythromycin in capsules (C), although both were significantly higher than the uncoated erythromycin/carbomer (A) in bioavailability.

What is claimed is:

1. A composition comprising from about 25% to about 95% of erythromycin or a derivative thereof, and from about 5% to about 75% of a carbomer.

2. A composition according to claim 1 wherein the erythromycin derivative is 6-O-methylerythromycin.

3. A composition comprising an ionic complex of from about 25% to about 95% of erythromycin or a derivative thereof, and from about 5% to about 75% of a carbomer.

4. A composition according to claim 3 wherein the erythromycin or derivative thereof is a compound of the formula

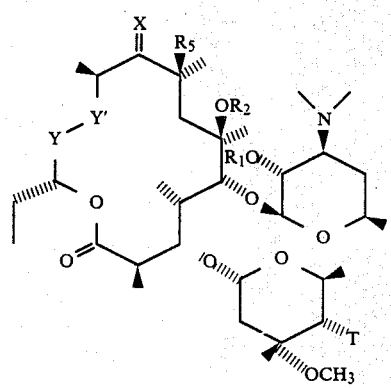

where $R_1$ is selected from hydroxyl, acyl of 2 to 20 carbon atoms, or trimethylsiloxyl, $R_2$ is hydrogen or methyl, T is hydrogen, —OH, alkoxy of 1 to 3 carbon atoms, —OCOR$_3$ or —OCONR$_3$R$_4$ where R$_3$ and R$_4$ are independently selected from hydrogen or alkyl of 1 to 12 carbon atoms, $R_5$ is hydrogen or halogen, X is O= or R$_6$ON= where R$_6$ is C$_1$ to C$_8$ substituted or unsubstituted alkyl, alkaryl or aryl and Y—Y' is

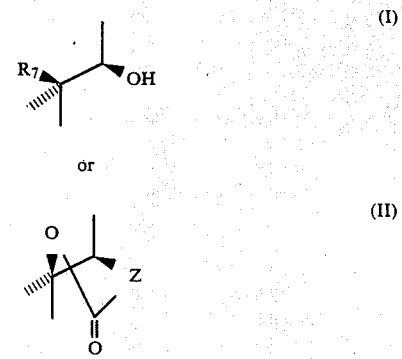

where $R_7$ is hydrogen or hydroxyl and Z is O= or R$_8$N= where R$_8$ is hydrogen, hydroxy, alkyl, alkoxy, substituted alkyl, aryl, sustituted aryl, acyl, or sulfonyl, or a pharmaceutically acceptable salt thereof.

5. A composition according to claim 4 wherein the erythromycin derivative is 6-O-methyl erythromycin A.

6. A composition comprising particles of an ionic complex of from about 25% to about 95% of erythromycin or a derivative thereof, and from about 5% to about 75% of a carbomer, the particles having a mean diameter of less than about 2000 microns.

7. A composition according to claim 6 wherein the particles have diameter of 420 microns or less.

8. A composition according to claim 7 wherein the particles have diameter of 297 microns or less.

9. A composition according to claim 6 wherein the particles have a coating of a polymer selected from ethyl cellulose, hydroxypropyl cellulose, hydroxypropylmethylcellulose, polyvinyl acetate phthalate, cellulose acetate phthalate, hydroxypropylmethylcellulose phthlate, and shellac, and mixtures thereof.

10. A pharmaceutical composition for oral administration comprising particles according to claim 6 suspended in a pharmaceutically acceptable liquid vehicle.

11. A suspension according to claim 10 wherein the particles have a coating of a polymer selected from ethyl cellulose, hydroxypropyl cellulose, hydroxypropylmethylcellulose, polyvinyl acetate phthalate, cellulose acetate phthalate, hydroxypropylmethylcellulose phthalate, and shellac, and mixtures thereof.

12. A granule for compression in the forming of tablets, comprising particles according to claim 6 and pharmaceutically acceptable tableting agents.

13. A method for making particles of an ionic complex of from about 25% to about 95% of erythromycin or a derivative thereof, and from about 5% to about 75% of a carbomer, comprising the steps of dispersing an erythromycin compound in a pharmaceutically acceptable organic solvent, dispersing a carbomer separately in a volume of said organic solvent, mixing the two dispersions to allow formation of a reaction product, removing at least a portion of the organic solvent, and diluting the remaining mixture with water.

14. A method according to claim 13 which further comprises the step of recovering the reaction product by filtration and drying the reaction product.

15. A method for making particles of an ionic complex of from about 25% to about 95% of erythromycin or a derivative thereof, and from about 5% to about 75% of a carbomer, comprising the steps of slurrying a mixture of the erythromyin or derivative and the carbomer in an organic solvent and then removing the solvent.

16. A chewable tablet made from granules according to claim 12.

* * * * *

UNITED STATES PATENT AND TRADEMARK OFFICE
CERTIFICATE OF CORRECTION

PATENT NO. : 4,808,411                         Page 1 of 2

DATED : February 28, 1989

INVENTOR(S) : Mou-Ying F. Lu, Saul Borodkin

It is certified that error appears in the above-identified patent and that said Letters Patent is hereby corrected as shown below:

Column 12, line 21: Replace "erythromyin" with --erythromycin--.

Column 2, lines 1-17: Add to the structural formula the bond which is highlighted in Formula A, attached hereto.

Column 10, lines 17-33: Add to the structural formula the bond which is highlighted in Formula B, attached hereto.

Signed and Sealed this

Seventh Day of May, 1991

Attest:

HARRY F. MANBECK, JR.

Attesting Officer            Commissioner of Patents and Trademarks

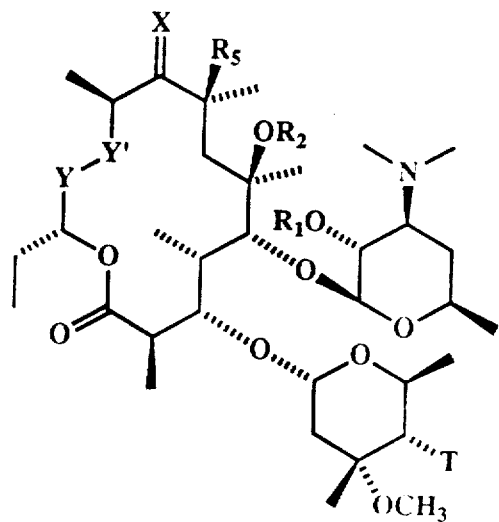
Formula A
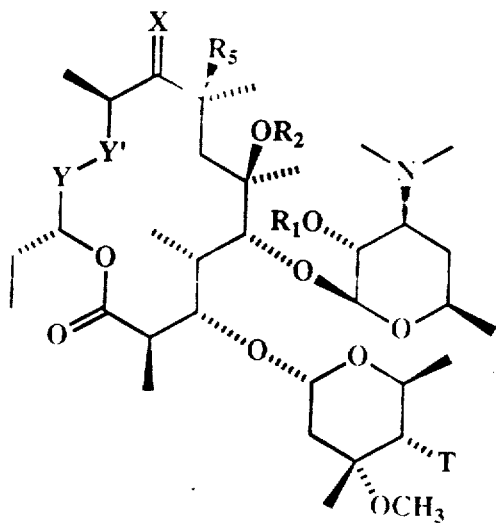
Formula B